United States Patent [19]

Maged

[11] Patent Number: 5,609,150

[45] Date of Patent: Mar. 11, 1997

[54] METHOD FOR DILATING RESPIRATORY PASSAGES

[76] Inventor: Jeffrey M. Maged, 46400 Benedict Dr., #105, Sterling, Va. 20164

[21] Appl. No.: 588,047

[22] Filed: Jan. 22, 1996

Related U.S. Application Data

[62] Division of Ser. No. 423,861, Apr. 18, 1995.

[51] Int. Cl.⁶ ........................................ A61L 15/07
[52] U.S. Cl. ...................... 128/201.18; 128/200.24; 128/898; 128/858; 606/204.45
[58] Field of Search ................... 128/898, 204.12, 128/207.18, DIG. 26, 858, 201.18, 200.24; 602/54, 58, 17, 74; 606/204.45, 204.15, 199

[56] References Cited

U.S. PATENT DOCUMENTS

| | | | |
|---|---|---|---|
| 1,839,606 | 1/1932 | Simmons . | |
| 4,719,909 | 1/1988 | Micchia et al. | 128/858 |
| 4,745,916 | 5/1988 | Seber | 128/155 |
| 5,284,469 | 2/1994 | Jasen et al. | 602/17 |
| 5,362,303 | 11/1994 | Jasen et al. | 606/204.45 |
| 5,476,091 | 12/1995 | Johnson | 128/200.24 |
| 5,533,499 | 7/1996 | Johnson | 128/200.24 |

FOREIGN PATENT DOCUMENTS

WO92/22340  12/1992  WIPO .

*Primary Examiner*—V. Millin
*Assistant Examiner*—V. Srivastava
*Attorney, Agent, or Firm*—Ronald P. Kananen

[57] ABSTRACT

In order to dilate nasal passages and to increase the ease with which respiration may be carried out through the nose, tape members are adhered to the wearer's face between a location adjacent the nose just below the medial infra orbital region and a location just inferior to the zygomatic ridge. The tape members maintain the nasal concha in a dilated state and markedly reduce the restriction to air flow.

12 Claims, 5 Drawing Sheets

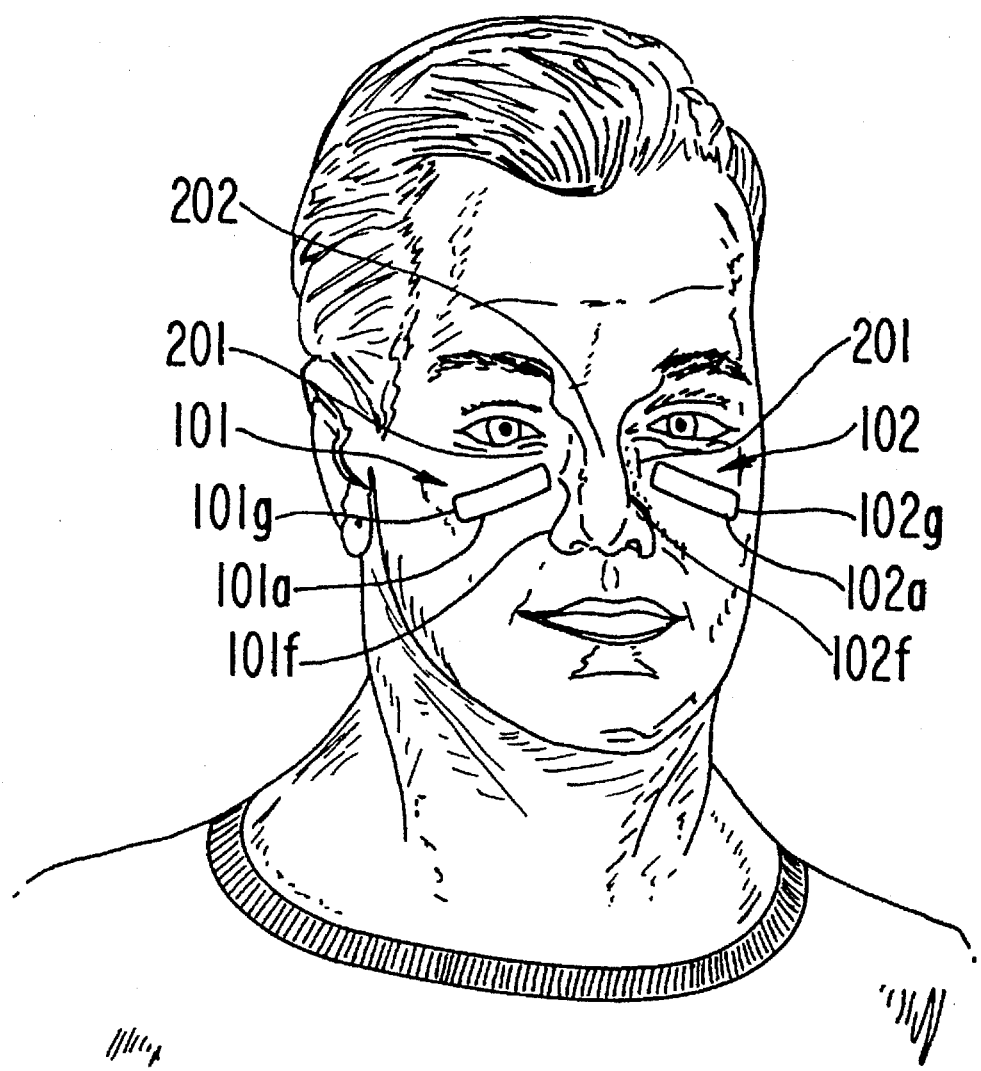

METHOD FOR DILATING RESPIRATORY PASSAGES

This application is a division of application Ser. No. 08/423,861 filed Apr. 18, 1995.

BACKGROUND OF THE INVENTION

1. Field of the Invention

The present invention related to an article which can be applied to the face of a user to facilitate respiratory activity. More specifically, the present invention relates to an article in form of a tape which can be applied to the face of a user on either side of the user's nose in a manner which opens the nasal concha and therefore reduces nasal air flow restriction and promotes easier breathing. Still more particularly, this invention relates to a method of facilitating respiratory activity.

2. Description of the Related Art

FIG. 1 shows an article 10 which can be applied to the nose in the illustrated manner and which is arranged to gently pull the nostril passages 12 open to dilate them. The article 10 is said to improve the ease with which the wearer can breathe through his or her nose. While this article exhibits certain merits such as being applicable to both athletes and persons who have difficulty breathing at night, it is only able to open the nostril passages. This arrangement is further such that it encounters the drawback that it can possibly interfere with the wearing of sunglasses, goggles or the like such as worn during ski competitions and the like. Accordingly, it remains an objective to improve upon the article 10 as will be seen from a review of this written description of the invention taken with the accompanying drawings.

SUMMARY OF THE INVENTION

It is an object of the present intention to provided an article which can be applied to the face of a user in a manner which reduces respiratory restriction and therefore eases breathing.

It is a further object of the invention to provide an article which can be applied to the face of a user in a manner which eases breathing through the nose while avoiding any obstacle to a comfortable wearing of goggles, sunglasses and the like.

It is a further object of the invention to provide an article which can be used to reduce glare by preventing reflection of light into the wearer's eyes while simultaneously increasing the ease with which breathing though the nose can be effected.

It is a further object to provide an article which opens or dilates the nasal concha as different from the nostrils, and which therefore reduces the resistance to air flow and facilitates breathing through the nose.

In brief, the above objects are achieved by tape members, preferably two, which are adhered to the wearer's face between a location adjacent the nose just below the medial infra orbital region, and a location just inferior to the zygomatic ridge. The tape members maintain the nasal concha in a dilated state and reduce restriction to air flow.

More specifically, a first aspect of the invention resides in an article comprising: a pair of dark-colored, non-reflective tapes which can be applied to the face of a user on either side of the nose in a manner which dilates the nasal concha and prevents annoying reflection of glare generating light into the wearer's eyes.

A second aspect of the invention resides in a nasal passage dilating article comprising: a pair tape members which are applied to the face of a user on either side of the nose in a manner which dilates the nasal concha; and glare-attenuating means for preventing annoying reflection of glare-generating light into the wearer's eyes, the glare-attenuating means comprising a dark-colored, non-reflective surface formed on said tape members.

A third aspect of the present invention resides in a method of increasing the ease with which breathing through the nose can be achieved comprising the steps of: adhering a first end of a tape adjacent the nose at a location just below the medial infra orbital region; pulling the tape to pull open and dilate a nasal concha and to establish a tension in the tape; and adhering a second end of the tape to wearer's face at a location just inferior to the zygomatic ridge in a manner which maintains the nasal concha in a dilated state.

A further aspect of the invention resides in the step of attenuating glare by providing the above mentioned tape with a dark colored non-reflective surface.

BRIEF DESCRIPTION OF THE DRAWINGS

The invention disclosed herein will become better understood as a detailed description is made of the preferred embodiments with reference to the appended drawings in which:

FIG. 2A is a perspective sketch showing a person wearing the article according to a first embodiment of the present invention;

DETAILED DESCRIPTION OF THE PREFERRED EMBODIMENT

Figure 2B:
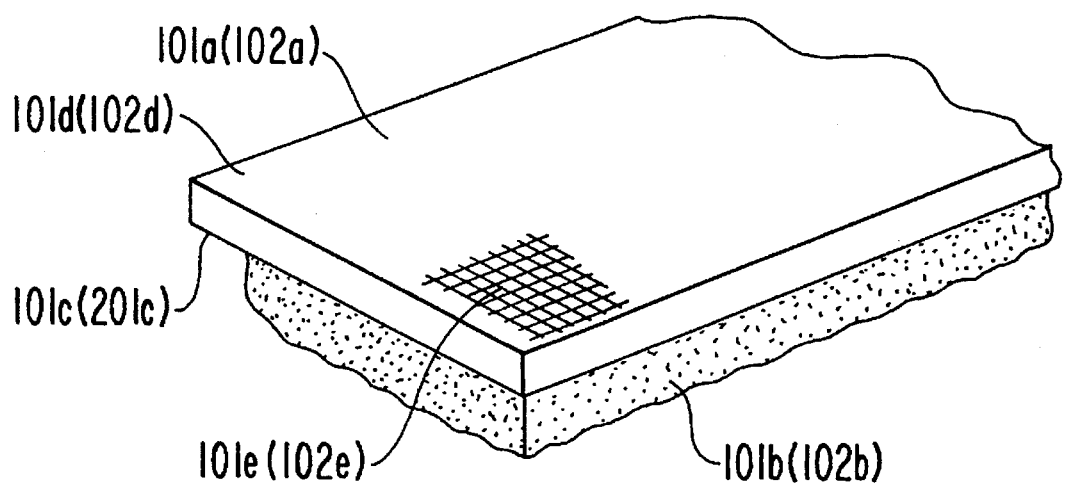
FIG. 2B is a perspective partially cut-away view showing a portion of one of the members which constitute the article shown in FIG. 2A.

FIGS. 2A and 2B show an embodiment of the invention. In this embodiment, the article comprises two members 101, 102, one for each side of the wearer's nose. Each of the members 101, 102 comprises a length of tape 101a, 102a which has a layer of adhesive 101b (102b) on the underside 101c (102c) (see FIG. 2B). The outer or upper side 101d, 102d of the tape 101a, 102a is preferably a non-reflective matte black or a similar dark color with a non-reflective finish 101e (102e). This allows the lengths of tape 101a, 102a to double as both a respiratory aid as well as a glare attenuation means which provides the same function attributed to the direct application of black coloring to the face.

As shown in FIG. 2A, the inboard ends 101f, 102f of the tapes 101a, 102a are each adhered to the face at a position 201 which is adjacent the nose 202 and just below the medial infra orbital region, while the outboard ends 101g, 102g are each adhered to the face at a location just inferior to the zygomatic ridge. With this disposition and with the above type of application the nasal concha are pulled open and dilated in a manner which notably reduces the resistance to air flow and permits improved breathing through the nose.

Figure 3:
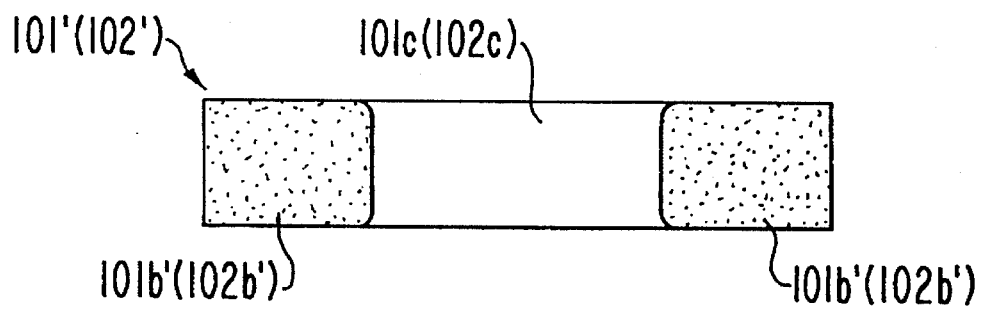
FIG. 3 is a plan view of an underside of an article according to a second embodiment of the present invention.

While the first embodiment of the invention features a continuous coating of adhesive 101a (102b) on the underside, it is possible in accordance with a second embodiment of the invention to provide adhesive 101b' (102a') only at the end portions of the tape members 101a' (102a') in the manner illustrated in FIG. 3.

Figure 4:
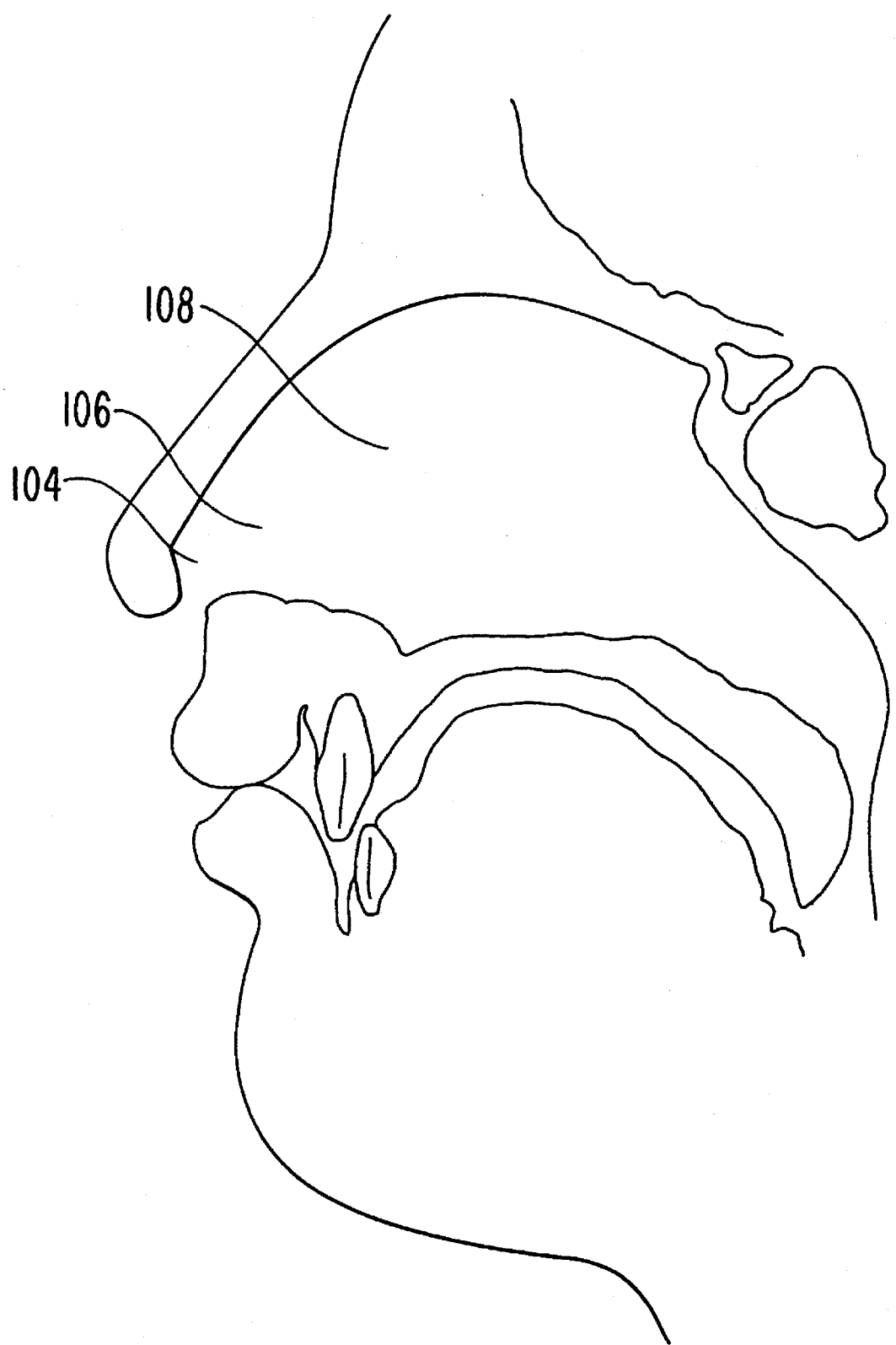
FIG. 4 is a sectional view showing air passages which exist within the interior of a human skull and which are effected by the present invention and the article shown in FIG. 1.

The effect of the present invention is such that rather than attempting to open the vestibule and limen nasi portions 204, 206 of the nose, the lengths of tape 101a, 102a which characterize the present invention are such as to effect the middle nasal concha 208. These portions are shown in FIG. 4. As will be appreciated, the volume of the concha portions of the respiratory passage is much larger than the passages defined by the nostrils (viz., the vestibule and limen portions 204, 206) and has a much larger effect on respiratory ease.

The invention is applied by firstly adhering a first end 101f, 102f of a tape member 101 (102) adjacent the nose 202 at a location 201 just below the medial infra orbital region, and end pulling the tape outwardly to produce a tractive force which pulls open and dilate a nasal concha 208. This, of course, produces a tension in the tape. Following this, while maintaining the tension the second end of the tape 101 is adhered to wearer's face at a location just inferior to the zygomatic ridge in a manner which maintains the nasal concha in a dilated state. A similar operation is performed on the other side of the nose.

Figure 1:
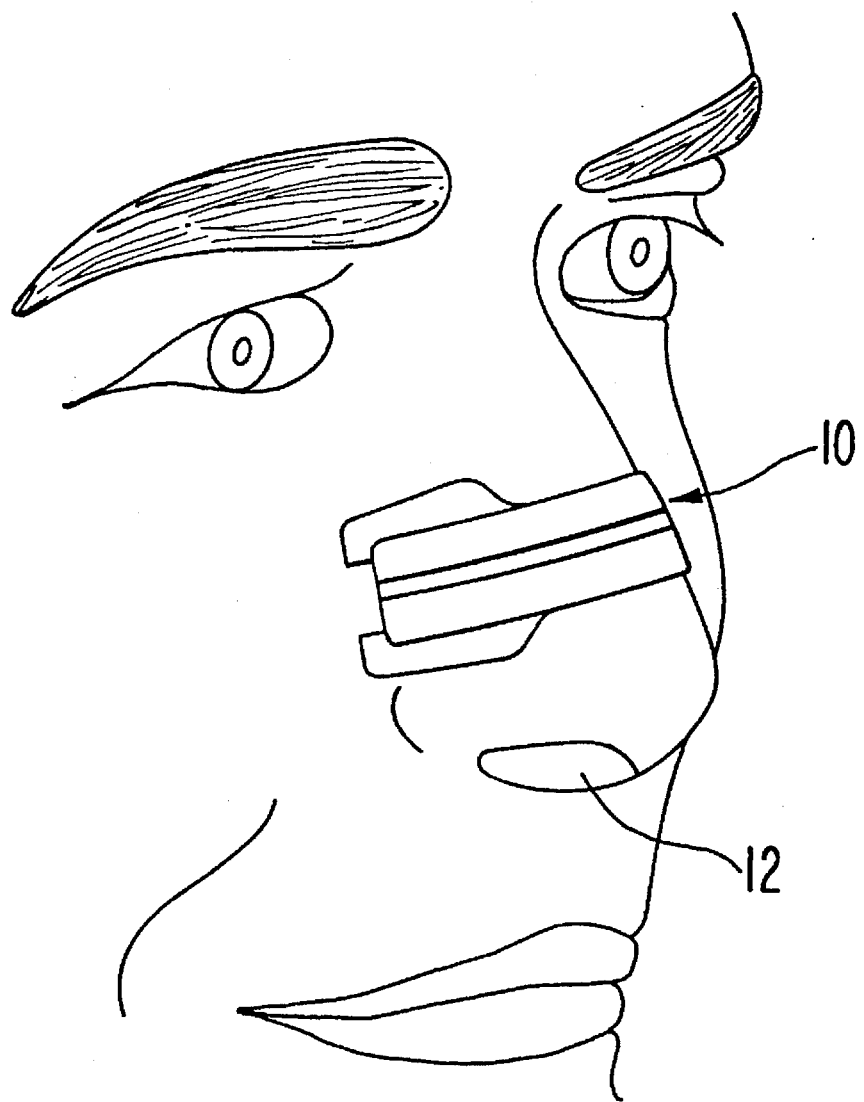
FIG. 1 is a perspective sketch showing the article referred to in the opening paragraphs of this disclosure.
Figure 5:
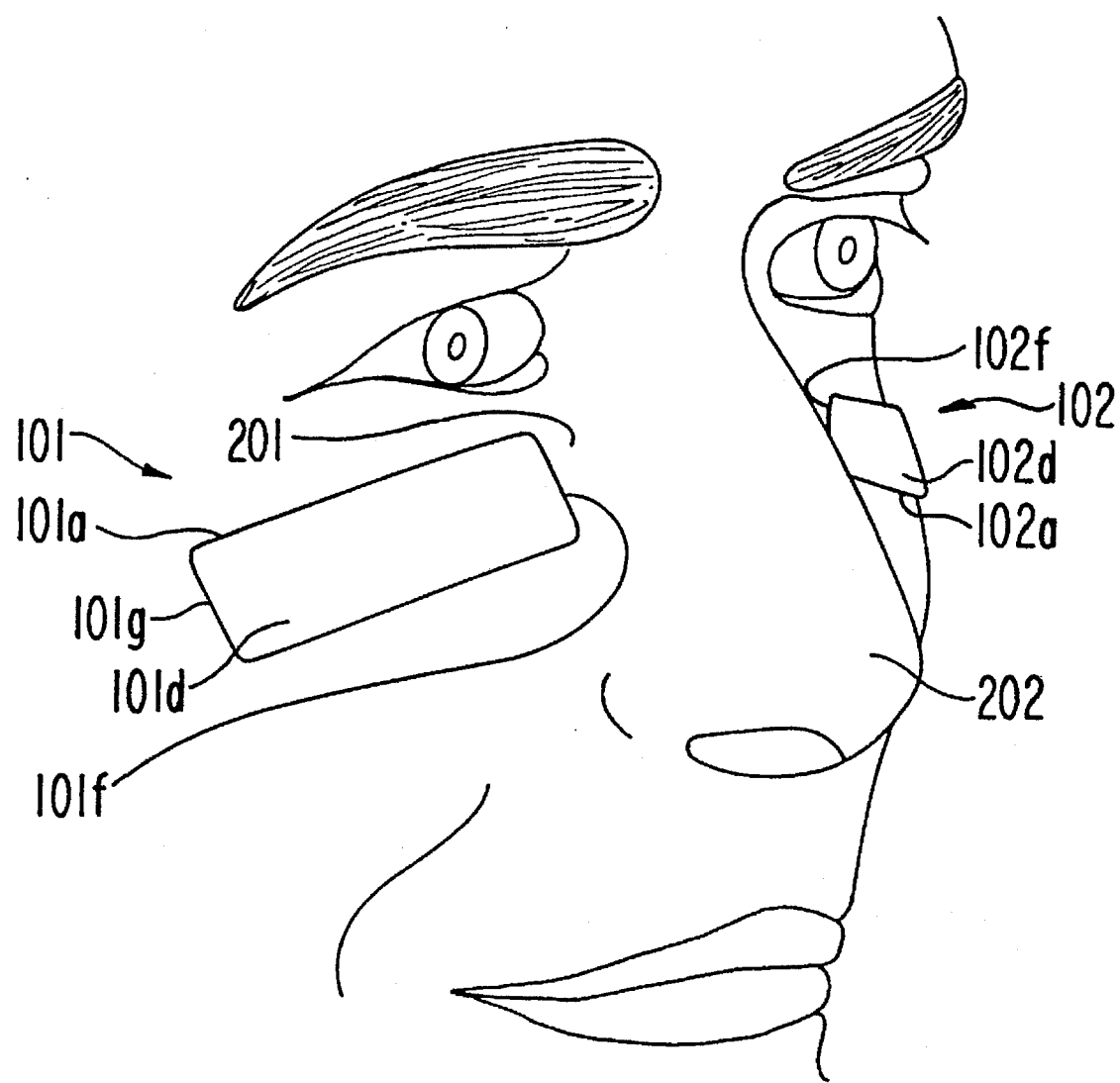
FIG. 5 is a perspective sketch showing an embodiment of the invention applied to a wearer's face.

As will be appreciated from a comparison of FIGS. 1 and 5, the present invention in addition providing a greater improvement in respiratory ease, is such as to avoid placing a layer on the nose which tends to interfere with the wearing of sunglasses, goggles and the like, and/or be partially visible and therefore annoying to the wearer, while simultaneously enabling glare to be attenuated through the use of tape members having the matte black surface 101e (102e).

The adhesive 101b (102b) which is used with the present invention is selected to be hypoallergenic so as to attenuate any possibility of an athletic wearer being caused any allergic reactions and the like type of skin irritation upon prolonged use.

In order to achieve optimum results for prolonged periods the invention should be applied before the wearer begins to sweat.

It will be appreciated that while only two embodiments of the invention have been discussed the various variations and modification which are possible will be self-evident to those skilled in the art to which this invention pertains. The present invention is therefore limited only by the appended claims.

What is claimed is:

1. A method of increasing the ease with which nasal breathing through a human nose can be improved, comprising the steps of:

adhering a first end of a tape member adjacent the nose at a location just below the medial infra orbital region;

pulling the tape member to pull open and dilate a nasal concha and to establish a tension in the tape; and adhering a second end of the tape member to a wearer's face at a location just inferior to the zygomatic ridge in a manner which maintains the tension in the tape member and therefore maintains the nasal concha in a dilated state.

2. A method as set forth in claim 1, further comprising the step of attenuating glare by providing said tape member with a dark colored non-reflective surface.

3. A method for easing respiratory activity in a human having a nose with nasal passages and a nasal concha, comprising:

adhering a first end of a first tape member to the face of a human wearer adjacent said nose at a location just below the medial infra orbital region in a manner which dilates the nasal concha and tensions said first tape member; and adhering a second end of said first tape member to the face of the human wearer at a location just inferior to the zygomatic ridge in a manner which maintains the tension in the first tape member and thus maintains the nasal concha in a dilated state.

4. The method as set forth in claim 3, wherein said first tape member has a length and an adhesive on at least a part of a side thereof, said first tape member being structurally applied by said adhesive to the face of the human wearer.

5. The method as set forth in claim 3, wherein said first tape member has a non-reflective surface on a side opposite said adhesive which prevents annoying reflection of glare-generating light into an eye of the wearer.

6. The method as set forth in claim 3, further including the additional steps of adhering a first end of a second tape member to the face of a human wearer adjacent said nose at a side of the face opposite that on which the first tape member is applied and at a location just below the medial infra orbital region in a manner which dilates the nasal concha and tensions said second tape member; and adhering a second end of said second tape member to the face of the human wearer at a location just inferior to the zygomatic ride in a manner which maintains the tension in the tape and thus maintains the nasal concha in a dilated state.

7. The method as set forth in claim 3 wherein, wherein said second tape member has a length and an adhesive on at least a part of a side thereof, said second tape member being applied by said adhesive to the face of the human wearer.

8. The method as set forth in claim 7, wherein said second tape member has a non-reflective surface on a side opposite said adhesive which prevents annoying reflection of glare-generating light into an eye of the wearer.

9. The method as set forth in claim 7 wherein each of said first and second tape members has an outboard end adapted to adhere to the face at a location inferior to the zygomatic ridge.

10. A method of using an article in combination with a wearer's face defining a nose with nasal passages and a nasal concha, comprising the steps of:

providing a pair of tape members each having a length and an adhesive on at least a part of a side thereof, applying each of said tape members respectively to the wearer's face on either side of the nose in a manner which dilates the nasal concha by adhering a first end of each of said tape members at a position adjacent the nose and below the medial infra orbital region such that the nasal concha are opened in a manner which reduces air flow resistance, and adhering a second end of each of said tape members to the face of the wearer at a location inferior to the zygomatic ridge.

11. The method as set forth in claim 10 wherein said adhesive is provided at substantially an entire surface of each of said tape members.

12. The method as set forth in claim 10 wherein each of said tape members has a dark colored non-reflective outer surface.

* * * * *